United States Patent [19]

Cavazza

[11] 4,299,842
[45] Nov. 10, 1981

[54] GUAIACOL ESTERS OF MERCAPTOPROPIONIC ACID DERIVATIVES, PROCESS FOR PREPARING SAME AND THERAPEUTICAL COMPOSITIONS COMPRISING SUCH ESTERS

[76] Inventor: Claudio Cavazza, 47, Viale Shakespeare, 00144 Rome, Italy

[21] Appl. No.: 103,785

[22] Filed: Dec. 14, 1979

[30] Foreign Application Priority Data

Dec. 21, 1978 [IT] Italy .................................. 52417 A/78

[51] Int. Cl.$^3$ .................. A61K 31/265; A61K 31/24; C07C 153/09; C07C 69/017
[52] U.S. Cl. ................................ 424/301; 260/455 R; 560/144; 560/137; 424/311
[58] Field of Search .................... 260/455 R; 424/301, 424/311; 560/144, 137

[56] References Cited

U.S. PATENT DOCUMENTS 4,108,886  8/1978  Ondetti .......................... 260/455 R Primary Examiner—Henry R. Jiles
Assistant Examiner—Robert C. Whittenbaugh
Attorney, Agent, or Firm—Ladas & Parry

[57] ABSTRACT

Esters with guaiacol of alpha- and beta-mercaptopropionylalanine and of alpha- and beta-mercaptopropionylglycine, their preparation process and their therapeutic use as mucolytic agents, are disclosed.

22 Claims, No Drawings

GUAIACOL ESTERS OF MERCAPTOPROPIONIC ACID DERIVATIVES, PROCESS FOR PREPARING SAME AND THERAPEUTICAL COMPOSITIONS COMPRISING SUCH ESTERS

BACKGROUND OF THE INVENTION

1. Field of the Invention

The invention relates to novel derivatives of mercaptopropionic acid and more particularly to esters with guaiacol (guaiacol esters) of alpha- and beta-mercaptopropionylalanine and of alpha- and beta-mercaptopropionylglycine, to the process for their preparation and to pharmaceutical compositions containing same.

The guaiacol esters of such mercaptopropionic acid derivatives are therapeutically useful as mucolytic agents.

2. Description of the Prior Art

To the best of the applicant's knowledge, the already known derivatives of mercaptopropionic acid more closely related to the compounds of the present invention are disclosed in the U.S. Pat. No. 3,246,025 the teachings of which are herein incorporated by reference.

The aforementioned patent discloses alpha- and beta-mercaptopropionylglycine, the amides and esters thereof, which are useful therapeutic agents for the treatment of drug intoxication and as antidotes in poisoning induced by mercury and arsenic compounds. In the preparation process as disclosed in the U.S. Patent, after having protected the sulfhydryl group of alpha- or beta-mercaptopropionic acid with an easily removable substituent in a successive reaction step, the carboxyl group is halogenated and the thus obtained acyl halide intermediate condensed with glycine to form the corresponding alpha- or beta-mercaptopropionylglycine derivative, from which the protective group is removed by conventional procedures. In order to obtain corresponding alpha- or beta-mercaptopropionylglycine amides or esters thereof, the acyl halide intermediate is made to react with either an already formed glycine amide or glycine ester respectively, instead of simply glycine.

The aforementioned U.S. Patent does not give any particular teachings regarding the nature of the protective substituents of the sulfhydryl group, the selection whereof is not evidently critical in view of the results to be accomplished, since it vaguely suggests that the sulfhydryl group is protected by a substituent that can easily be removed in a succeeding reaction, and confines the examples to benzyl, acetyl, nitrobenzyl and nitrobenzoyl. Also in regard to the removal of the protective group and the consequent recovery of the sulfhydryl the U.S. Patent does not disclose the specifically critical conditions it uses, ranging from the use of sodium metal in liquid ammonia (at approximately −50° C.) to the use of concentrated ammonia, sodium hydroxide or barium hydroxide.

SUMMARY

In accordance with the present invention, there is provided a novel mucolytically active guaiacol ester of a mercaptopropionic acid derivative, selected from the group represented by the general formulae (I and (II):

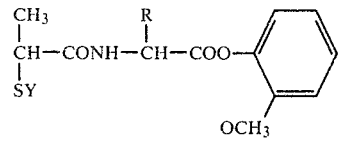

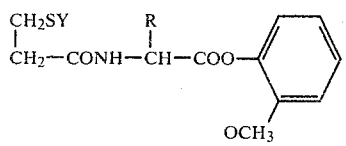

wherein R is selected from the group consisting of hydrogen and methyl, and Y is selected from the group consisting of hydrogen and an acyl radical, preferably acetyl, benzoyl or methoxycarbonyl. Therefore, the compounds listed below are specifically included within the scope of the present invention:

alpha-mercaptopropionylglycine guaiacol ester
beta-mercaptopropionylglycine guaiacol ester
alpha-mercaptopropionylalanine guaiacol ester
beta-mercaptopropionylalanine guaiacol ester
alpha-acetylmercaptopropionylglycine guaiacol ester
beta-acetylmercaptopropionylglycine guaiacol ester
alpha-acetylmercaptopropionylalanine guaiacol ester
beta-acetylmercaptopropionylalanine guaiacol ester
alpha-benzoylmercaptopropionylglycine guaiacol ester
beta-benzoylmercaptopropionylglycine guaiacol ester
alpha-benzoylmercaptopropionylalanine guaiacol ester
beta-benzoylmercaptopropionylalanine guaiacol ester
alpha-methoxycarbonylmercaptopropionylglycine guaiacol ester
beta-methoxycarbonylmercaptopropionylglycine guaiacol ester
alpha-methoxycarbonylmercaptopropionylalanine guaiacol ester
beta-methoxycarbonylmercaptopropionylalanine guaiacol ester A guaiacol ester having the formula,

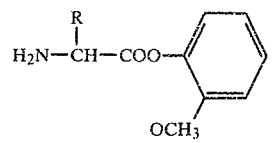

wherein R has the above-described meaning, also falls within the scope of the present invention as an intermediate in the preparation of the aforesaid guaiacol esters (I) and (II).

For the general operative guidelines of some steps of the process for preparing the novel guaiacol esters of the present invention the teachings of the prior art may be referred to, particularly in relation to the formation of the peptide bond between the mercaptopropionic portion and the glycine or alanine portion of the molecule. In this regard reference is made to "Peptides and Amino Acids", Kenneth D. Kopple, W. A. Benjamin, Inc. (1966) and "Chemistry of the Amino Acids" (vol. III), J. P. Greenstein and M. Winitz, Wiley, New York (1961). However, it is to be borne in mind that the preparation processes disclosed and claimed in the present specification have never been described before, as a whole, in the prior art, and that the preparation of the guaiacol ester of formulae (I) and (II) requires the use of particular operative conditions which also fall within the scope of the present invention.

It has in effect been found that the selection of a suitable protective substituent for the sulfhydryl group, and likewise the operative conditions for removing such protective substituent, is absolutely critical in the present invention.

Such a protective substituent and specific operative conditions for removal thereof are not automatically obtained from the prior art. In particular, the protective substituents and procedures for removing such substituents disclosed in the U.S. Pat. No. 3,246,025 prove to be totally unsuitable for obtaining the compounds of the present invention.

In order to prepare the compounds (I) and (II) it is indispensable to have a protective group of the sulfhydryl group, the removal of which is possible without causing damage to the guaiacol ester which is highly sensitive to the bases and acids as well as to nucleophilic reagents, such as ammonia and amines, in that the guaiacol nucleus tends to activate the carbonyl group toward these types of attack.

According to the present invention the process for preparing a guaiacol ester of a mercaptopropionic acid derivative, selected from the group represented by the general formulae (I) and (II)

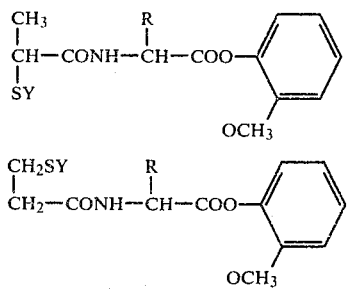

wherein:
R is selected from the group consisting of hydrogen and methyl; and
Y is selected from the group consisting of hydrogen and an acyl radical,
comprises preparing in a known per se manner a compound of the following formula IA or IIA

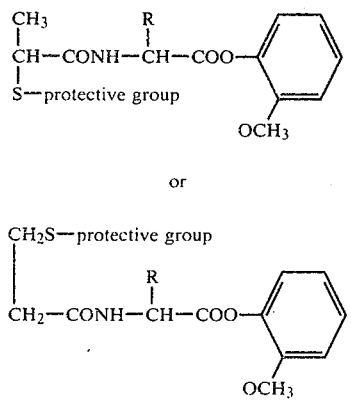

wherein R is as defined above and is characterized by:
(a) removing the protective group from the compound of the foregoing formula IA or IIA by reaction of said compound of formula IA or IIA with an acid environment;
(b) and then reacting the product produced in step (a) with an acylating agent when Y in the product of formula I or II is an acyl radical.

It has been found that suitable protective groups are p-methoxybenzyl and triphenylmethyl (trityl), this latter being particularly preferred.

The scope of the present invention lastly covers a pharmaceutical composition comprising, as a therapeutically active ingredient, such a quantity of one or more of the guaiacol esters from formulae (I) and (II) so as to produce a mucolytic effect, and a therapeutic method comprising administration to subjects having a respiratory disease and in need of a mucolytic agent of the above composition.

DESCRIPTION OF THE PREFERRED EMBODIMENTS

In the present invention the novel guaiacol esters of formulae (I) and (II) are preferably prepared according to the two synthesis schemes which are illustrated in detail hereinbelow. For the sake of simplicity in the schemes the alpha-mercaptopropionic acid reaction is shown with trityl being illustrated as the protective group; it is, however, evident that the same equally applies to beta-mercaptopropionic acid and to the other mentioned protective group.

The protection of the sulfhydryl group of mercaptopropionic acid with one of the aforesaid protective groups, preferably trityl, is common to the synthesis procedures illustrated in the schemes below, and essential—as already suggested—in order to obtain the desired compounds. For such a purpose, mercaptopropionic acid is mixed with triphenylcarbinol and to the mixture trifluoroacetic acid is added. The resultant solution is maintained under stirring at room temperature. Successively, the excess of trifluoroacetic acid is removed by evaporation at reduced pressure and the residue is taken up, using, for instance, ethyl ether. The pure compound is isolated by cristallization, for example by means of methylene chloride-hexane.

According to the first process, S-trityl-alpha-mercaptopropionic acid is converted to acyl halide which when condensed with glycine or alanine yields S-trityl-alpha-mercaptopropionylglycine or S-trityl-alpha-mercaptopropionylalanine, respectively. The last two compounds are reacted, according to the mixed anhydride method, with ethyl or isobutyl chlorocarbonate and the thus obtained anhydrides condensed with guaiacol, thereby obtaining the respective esters which after the removal of the protective group yield the desired guaiacol esters. This procedure is illustrated in the following synthesis scheme 1.

SYNTHESIS SCHEME 1

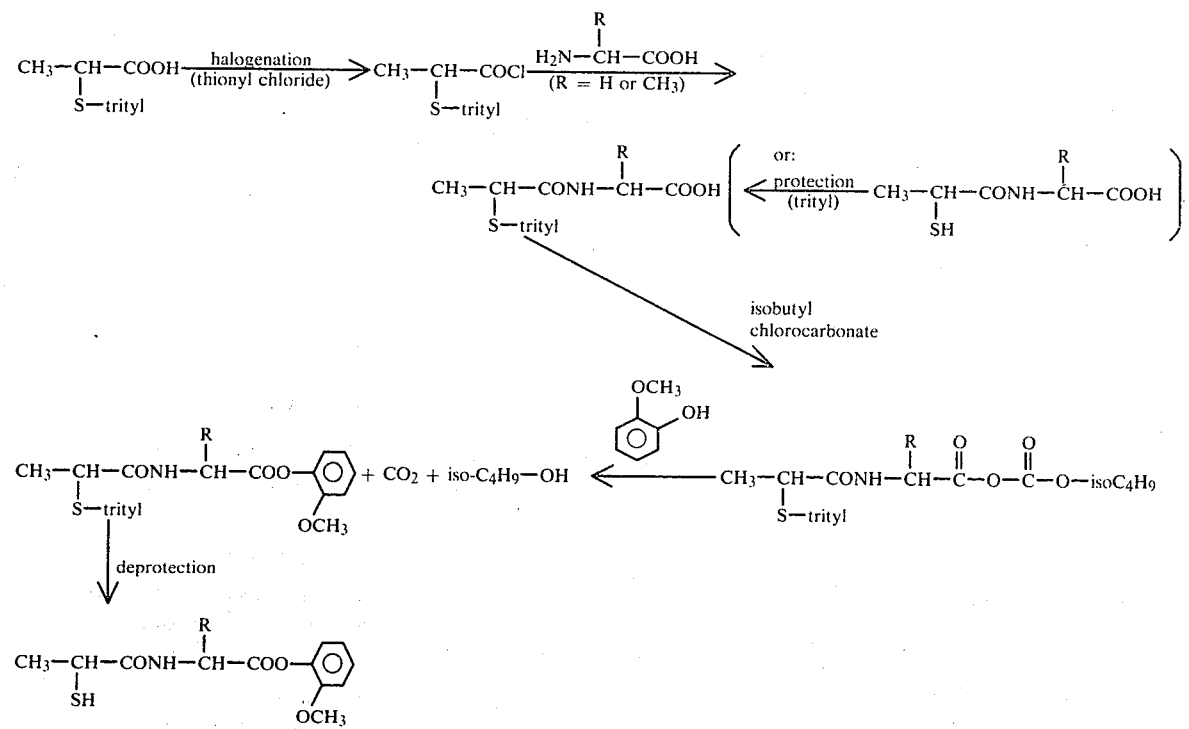

According to the second process which is particularly preferred, the glycine (or alanine) amino group is firstly inactivated (or protected) by reacting with a suitable inactivating agent, thereby obtaining, for example, the corresponding N-carbobenzyloxy derivative which in turn is reacted with a guaiacol solution in the presence of ethyl or isobutyl chlorocarbonate. The thus obtained N-carbobenzyloxyglycine (or alanine) guaiacol ester is then hydrogenated in the presence of hydrochloric acid, thereby obtaining glycine (or alanine) guaiacol ester hydrochloride. Other suitable protective agents for inactivating the glycine or alanine amino group are disclosed in "Chemistry of the Amino Acids" (vol. II), J. P. Greenstein and M. Winitz, Wiley, New York (1961).

On the other hand, S-trityl-mercaptopropionic acid is firstly converted according to the mixed anhydride method by reaction with ethyl or isobutyl chlorocarbonate to the corresponding anhydride which may undergo nucleophilic attack by the amino group of glycine guaiacol ester or alanine guaiacol ester.

The protective group is then removed from the S-trityl-mercaptopropionylalanine (or glycine) guaiacol ester, thereby obtaining the desired compound.

This process is illustrated in the following synthesis scheme 2.

SYNTHESIS SCHEME 2

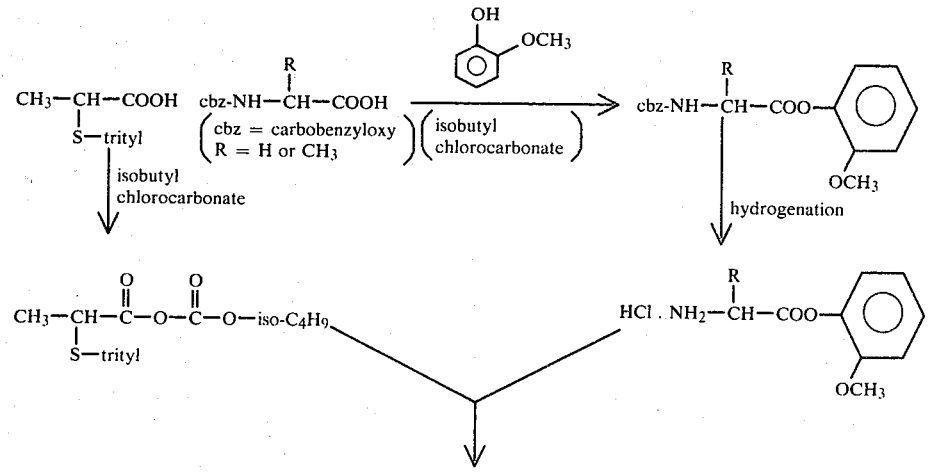

-continued
SYNTHESIS SCHEME 2

$$CH_3-CH(S-trityl)-CONH-CH(R)-COO-C_6H_4-OCH_3 \xrightarrow{deprotection} CH_3-CH(SH)-CONH-CH(R^1)-COO-C_6H_4-OCH_3 + CO_2 + iso\text{-}C_4H_9-OH$$

As has already been suggested, the removal of the protective group requires particular operative conditions which are not automatically drawn from the prior art. In particular, none of the reactions disclosed in the U.S. Pat. No. 3,346,025 requiring the use of an alkaline environment would enable the protective group to be removed from the sulfhydryl group without a simultaneous splitting of the guaiacol ester by hydrolysis or ammonolysis.

It has in fact been found that the removal of the protective group not only must occur in acid and not in basic conditions, but also requires different conditions according to whether the protected sulfhydryl group is in alpha or in beta position with respect to the amide bond.

Trifluoroacetic acid is preferably used in the case of alpha-mercapto (protected) propionylalanine and alpha-mercapto (protected) propionylglycine guaiacol esters.

In the case of beta-mercapto (protected) propionylalanine and beta-mercapto (protected) propionylglycine guaiacol esters, treatment is to be carried out with mercuric chloride in trifluoroacetic acid which enables the trityl group to be removed in the form of chloride with the consequent precipitation of the mercurial; beta-mercaptopropionylglycine guaiacol ester and beta-mercaptopropionylalanine guaiacol ester are successively released by the corresponding mercuric salt by means of treatment with hydrogen sulfide in an alkanol, preferably methanol.

For the preparation of the derivatives acylated at the sulfhydryl group acylation of the guaiacol ester acids of alpha- or beta-mercaptopropionylglycine and alpha- or beta-mercaptopropionylalanine can be carried out with anhydrides or chlorides.

Alternatively, guaiacol esters acylated at the sulfhydryl group can be prepared starting from alpha-acyl- or beta-acyl-mercaptopropionic acid and thereafter proceeding according to scheme 1 or 2.

The following examples further illustrate this invention, but it is to be understood that they should not be so construed as to limit the scope of the invention. The examples marked with letters (A–N) relate to the preparation of intermediate compounds, whereas these marked with numerals (1–7) relate to the preparation of the guaiacol ester end products.

EXAMPLES

Preparation of Intermediate Compounds (1) Intermediates common to synthesis schemes 1 and 2

Example A

S-trityl-alpha-mercaptopropionic acid

To a mixture of triphenylcarbinol (13 g; 0.05 moles) and alpha-mercaptopropionic acid (5.3 g; 0.05 moles) 50 ml of trifluoroacetic acids were added.

The red solution thereby obtained was stirred at room temperature for 15 minutes.

The excess of trifluoroacetic acid was removed by evaporation under reduced pressure, and the residue was taken up with ethyl ether. 14–16 grams of the pure compound were obtained.

M.P. 149°–150° C. (methylene chloride-hexane).

Example B

S-trityl-beta-mercaptopropionic acid

Example A was repeated in exactly the same manner substituting beta-mercaptopropionic acid for alpha-mercaptopropionic acid, and comparable yields were obtained.

M.P. 204°–205° C. (dioxane)

Example C

S-(p)-methoxybenzyl-beta-mercaptopropionic acid

To an aqueous suspension of beta-mercaptopropionic acid (16 g in 130 ml of water) at 0°–3° C., p-methoxybenzyl chloride (26.99 g, all at once) and $NaHCO_3$ (14.48 g, portionwise) were added. A crystalline precipitate thus formed. After 2 hours, the pH of the mixture was adjusted to 2 with aqueous HCl and exctracted with ethyl ether. This last phase was extracted with a saturated solution of $NaHCO_3$.

The aqueous solution of sodium S-p-methoxybenzyl-beta-mercaptopropionate was extracted with ethyl ether and then acidified to Red Congo with concentrated HCl. The precipitate thereby obtained was filtered off and dried in vacuo.

M.P. 73°74° C.

(2) Preparation of intermediate compounds according to the synthesis scheme 1

Example D

S-trityl-alpha-mercaptopropionylglycine (a) To a benzene solution of S-trityl-alpha-mercaptopropionic acid (8.1 g; 0.02 moles) thionyl chloride (2.38 g; 0.02 moles) was added. After the mixture was kept at boiling point for 2 hours, the mixture was dried in vacuo. The residue was dissolved in dioxane (25 ml) and added to a solution of glycine (1.5 g; 0.02 moles) and MgO (1.21 g; 0.03 moles) in 75 ml of water. After 2 hours stirring at room temperature, the resulting mixture was acidified with 1 N HCl. Upon dilution with water a white precipitate formed which when dried and recrystallized (ether) had M.P. 179°–180° C.

(b) To a solution of alpha-mercaptopropionyl glycine (50 g; 0.307 moles) in 300 ml of trifluoroacetic acid, were added 79.9 g (0.307 moles) of triphenylcarbinol. The thus obtained solution was kept under stirring at room temperature for 15 minutes. The excess of trifluoroacetic acid was removed by evaporation and the residue taken up with ether. Filtration yielded a white solid, which was then washed with ether and dried in vacuo to constant weight.
M.P. 179°–180° C.

Example E

S-trityl-alpha-mercaptopropionylglycine guaiacol ester

To a suspension of S-trityl-alpha-mercaptopropionylglycine (81 g) in methylene chloride (500 ml), triethylamine (29 ml; 1.05 eq) was added at 0° C. To the solution thus obtained, cooled to −3° C. through −5° C., a solution of isobutyl chlorocarbonate (27.5 ml; 1.05 eq) in methylene chloride (200 ml) was added over a 10 minute period. Upon completion of the addition, the mixture was stirred for 20 minutes at −3° C. through −5° C. To this mixture a solution of guaiacol (26 g; 1.05 eq) in methylene chloride (200 ml) containing triethylamine (29 ml) was added over a 15-minute period.

After stirring for 15 minutes at −5° C., the solution was allowed to stand overnight at room temperature. The solution was then washed successively with water, 1 N HCl, water to neutrality and lastly the organic phase thus obtained was dried with sodium sulfate. After solvent evaporation, the resulting oil was taken up with hexane and yielded a white solid which would be re-crystallized from acetone-hexane. 80 grams of S-trityl-alpha-mercaptopropionylglycine guaiacol ester (M.P. 161°–162° C.) were obtained.

Example F

S-trityl-alpha-mercaptopropionyl alanine guaiacol ester

The title compound was prepared by using the same procedures as those disclosed in the synthesis of S-trityl-alpha-mercaptopropionylglycine guaiacol ester (Example E). Comparable yields were obtained.
M.P. 167°–168° C. (ethyl acetate).

(3) Preparation of intermediate compounds according to synthesis scheme 2

Example G

Glycine guaiacol ester hydrochloride.

To a solution at −3° C. of N-carbobenzyloxyglycine (10 g; 5.7 m moles) in methylene chloride (100 ml) and triethylamine (7.25 ml), isobutyl chlorocarbonate (6.82 ml; 1.1 eq) in the same solvent (40 ml) was added over a 5-minute period. After stirring at the same temperature for 20 minutes, a guaiacol solution (5.93 g; 1.0 eq) in methylene chloride (40 ml) containing triethylamine (7.25 ml; 1.1 eq) was added. After 1 hour at −5° C., the temperature was allowed to rise spontaneously to 20° C., then water was added and the organic phase was washed sequentially with water, 1 N HCl, water, 2 N NaOH and water to neutrality. The resulting phase was dried with sodium sulfate and, after solvent evaporation, N-carbobenzyloxyglycine guaiacol ester as an oil was obtained.

A solution of this last compound (10 g) in absolute ethanol (50 ml), after addition of 0.975 N HCl in ethanol (36 ml) and 10% palladium on carbon (1 g), was hydrogenated at room temperature and atmospheric pressure. After catalyst filtration on celite and evaporation to dryness, upon crystallization from acetone-ethanol 4.4 grams of the title hydrochloride having M.P. 171°–172° C. were obtained.

Example H

Alanine guaiacol ester hydrochloride

The title compound was prepared from N-carbobenzyloxy alanine using the same procedures as those disclosed for the synthesis of glycine guaiacol ester hydrochloride.

Alanine guaiacol ester hydrochloride, crystallized from acetone-ethanol, had M.P. 196°–197° C.

Example I

S-trityl-alpha-mercaptopropionyl glycine guaiacol ester

To a suspension of 0° C. of S-trityl-alpha-mercaptopropionic acid (3.48 g; 10 m moles) in methylene chloride (20 ml), triethylamine (1.5 ml; 11 m moles) was added. To this suspension, a solution of isobutyl chlorocarbonate (1.43 ml; 11 m moles) in methylene chloride (6 ml) was added at −3° C. through −5° C. The resulting mixture was stirred at the same temperature for 20 minutes. To the mixed anhydride thus obtained, the solution of the glycine guaiacol ester was added, which has been prepared in situ from the corresponding hydrochloride (2.18 g) in methylene chloride (20 ml) containing trithylamine (3.04 ml).

The mixture was allowed to stand under stirring at −3° C. through −5° C. for 40 minutes and subsequently at room temperature for 2 hours. The reaction mixture was washed sequentially with water, 1 N HCl and water, dried over sodium sulfate and evaporated to dryness. A residue was obtained that, upon crystallization from acetone-hexane, yielded 3.75 grams of a compound having M.P. 161°–162° C.

Example J

S-trityl-alpha-mercaptopropionylalanine guaiacol ester

The title compound was prepared by using the same procedures as those disclosed for the synthesis of S-trityl-alpha-mercaptopropionyl glycine guaiacol ester (Example I), obtaining comparable yields.
M.P. 167°–169° C. (ethyl acetate)

Example K

S-trityl-beta-mercaptopropionyl glycine guaiacol ester

To a solution of triethylammonium S-trityl-beta-mercaptopropionate (10 m moles) in methylene chloride (20 ml), a solution of isobutyl chlorocarbonate (1.43 ml; 11 m moles) in methylene chloride (8 ml) was added. After 20 minutes at the temperature of −3° C. through −5° C. a solution of glycine guaiacol ester prepared in situ from the corresponding hydrochloride (2.18 g) in methylene chloride (20 ml) containing triethylamine (3.04 ml; 22 m moles) was added. The mixture was allowed to stand at the same temperature for 40 minutes and subsequently at room temperature for 2 hours. The reaction mixture, upon treatment as indicated for the preparation in Example I of S-trityl-alpha-mercaptopropionyl glycine guaiacol ester, yielded a residue which, upon deposition on florisil (IR=10) by passing a solution in $CH_2Cl_2$ over florisil followed by elution with methylene chloride: methanol 99.5:0.5 and crystallization from ethyl acetate-hexane gave 3.3 grams of the title compound having M.P. 98.5°–100.5° C.

Example L

S-trityl-beta-mercaptopropionyl alanine guaiacol ester

The title compound was prepared with the same procedures as those indicated in Example K for the synthesis of S-trityl-beta-mercaptopropionyl glycine guaiacol ester, using alanine guaiacol ester hydrochloride.

M.P. 140° C. (dec.) (Acetone-hexane).

Example M

S-(p)-methoxybenzyl-beta-mercaptopropionyl alanine guaiacol ester

To a solution at −3° C. of S-(p)-methoxybenzyl-beta-mercaptopropionic acid (2.26 g; 10 m moles) in methylene chloride (20 ml) containing triethylamine (1.52 ml; 11 m moles), a solution of isobutyl chloro carbonate (1.43 ml; 11 m moles) in $CH_2Cl_2$ (8 ml) was added. After 20 minutes at a temperature of −3° C. through −5° C., a solution of alanine guaiacol ester prepared from the corresponding hydrochloride (2.32 g) in methylene chloride (20 ml) containing triethylamine (3.04 ml) was added.

The mixture was allowed to stand under stirring at 0° C. for 3 hours. Lastly, the reaction mixture was washed twice with 1 N HCl, then with water to neutrality, dried with $Na_2SO_4$ and evaporated. The product thus obtained can be subjected as such to the reaction for removing the protective group of the sulfhydryl group.

Example N

S-(p)-methoxybenzyl-beta-mercaptopropionyl glycine guaiacol ester

The title compound was prepared with the same procedures as those indicated for the synthesis of S-(p)-methoxybenzyl-beta-mercaptopropionyl alanine guaiacol ester (Example M).

PREPARATION OF THE GUAIACOL ESTERS

Example 1

Alpha-mercaptopropionyl glycine guaiacol ester

A solution of S-trityl-alpha-mercaptopropionyl glycine guaiacol ester (1 g) in trifluoroacetic acid (5 ml) was stirred at room temperature for 15 minutes; subsequently, this solution was added dropwise to 150 ml of water kept at 1°–3° C.

The white precipitate thus obtained, consisting of triphenylcarbinol, was filtered off and the water solution was extracted with methylene chloride. After the organic extracts had been dried with sodium sulfate, the product was evaporated to dryness. The residue thus obtained, taken up with ether and filtered, gave 430 mg of the title compound having M.P. 74°–75° C. (ethyl ether).

Example 2

Alpha-mercaptopropionylalanine guaiacol ester

The title compound was prepared from the corresponding S-trityl-derivative with the same procedures as those disclosed for the preparation of alpha-mercapto propionyl glycine guaiacol ester, using S-trityl-alpha-mercaptopropionyl alanine guaiacol ester as the starting material.

M.P. 112°–114° C. (dichloromethane-hexane)

Example 3

Beta-mercaptopropionylalanine guaiacol ester (A) To a solution of S-trityl-beta-mercaptopropionyl alanine guaiacol ester (525 mg) in trifluoroacetic acid (10 ml), 550 mg of mercuric chloride were added at room temperature.

After 5 hours under stirring at room temperature, the suspension thus obtained was evaporated to dryness in vacuo. The residue was taken up with ethyl ether and the mercurial precipitate was filtered, and washed the insoluble phase with another portion of ethyl ether.

The mercurial precipitate was suspended in methanol (3 ml) and hydrogen sulfide was bubbled therein for few minutes. The mercuric sulfide was filtered and the filtrate was evaporated to dryness in vacuo.

N.M.R. ($CDCl_3$) δ:1.59 (3H,d,$CH_3CH$, J=7 Hz), 2.33–3.15 (4H,m, $CH_2—CH_2SH$), 3.76 (3H,s, $OCH_3$), 4.66–5.16 (1H,m, $CHCH_3$), 6.32 (1H, s broad, SH), 6.80–7.50 (4H,m,ArH).

(B) 550 mg of mercuric chloride were added at room temperature to a solution of S-(p)-methoxybenzyl-beta-mercaptopropionyl alanine guaiacol ester (403 mg) prepared as in Example M in trifluoroacetic acid (10 ml). After 5 hours under stirring at room temperature the suspension thus obtained was evaporated to dryness and the solid residue was suspended in ether. The residue was filtered and washed several times with ethyl ether.

The mercurial residue was suspended in methanol (3 ml) and hydrogen sulfide was bubbled therein for few minutes. The mercuric sulfide which formed was filtered, washed with ethyl ether-methanol, and the combined filtrates were then evaporated to dryness in vacuo. N.M.R. analysis showed that the residue had the same characteristic as those exhibited by the compound obtained with the process (A).

Example 4

Beta-mercaptopropionyl glycine guaiacol ester

The title compound was prepared from S-trityl-beta-mercaptopropionyl glycine guaiacol ester or S-(p)-methoxybenzyl-beta-mercaptopropionyl glycine guaiacol ester under the same conditions as those disclosed for the synthesis of beta-mercaptopropionyl alanine guaiacol ester.

Example 5

Alpha-methoxycarbonylmercaptopropionyl glycine guaiacol ester

A solution of methyl chloroformate (0.56 g; 5.94 m moles) in 0.9 ml of dimethoxyethane at 0° C. was added to a solution of alpha-mercaptopropionyl glycine guaiacol ester (1 g; 3.71 m moles) in pyridine (5 ml).

After 30 minutes at 0° C., water was poured in the resulting solution, which was then extracted with methylene chloride. The organic extracts were firstly washed with 1 N HCl, then with water, dried over sodium sulfate and lastly evaporated.

N.M.R. (CDCl$_3$) δ:1.52 (3H,d,CH$_3$CH,J=7.5 Hz), 3.90 (1H,q, CHCH$_3$, J=7.5 Hz), 3.76 (6H,s,OCH$_3$), 4.30 (2H,d,CH$_2$NH, J=5.5 Hz), 6.65–7.4 (4H,m,ArH)

I.R.: 3400–3300, 3070, 1680, 1655, 1755 cm$^{-1}$.

Example 6

Alpha-acetylmercaptopropionyl glycine guaiacol ester (A) Acetic anhydride (1 ml) was added to a solution of alphamercaptopropionylglycine guaiacol ester (1 g; 3.71 m moles) in pyridine (5 ml). After 18 hours at room temperature the mixture was poured on ice and extracted with methylene chloride, dried and evaporated. The residue showed at I.R. analysis bands at 3300–3400, 3070, 1775, 1690, 1680–1655 cm$^{-1}$ N.M.R. (CDCl$_3$) δ:1.48(3H,d,CH$_3$CH, J=7.5 Hz), 2.30 (3H,s,CH$_3$CO), 3.77 (3H,s,OCH$_3$), 4.15 (1H,q,CHCH$_3$,J=7.5 Hz), 4.27 (2H,d,CH$_2$NH, J=5.5 Hz), 6.65–7.40 (4H,m,ArH)

(B) Triethylamine (3.04 ml) was added to a solution of alpha-acetylmercaptopropionic acid (2.96 g) in methylene chloride (40 ml). At −3° C. through −5° C. a solution of isobutyl chlorocarbonate (2.87 ml) in methylene chloride (14 ml) was added.

The mixture was stirred at the same temperature for 10 minutes and then a solution of glycine guaiacol ester prepared in situ from the corresponding hydrochloride (4.36 g) in methylene chloride (30 ml) containing triethylamine (6.08 ml) was added thereto.

The mixture was stirred until the temperature rose up to room temperature (2 hours). The reaction mixture was washed sequentially with water, 1 N HCl, water and then dried and evaporated.

The residue has the same spectroscopical characteristics as those of the compound obtained in process (A).

Example 7

Alpha-benzoylmercaptopropionylglycine guaiacol ester (A) Benzoyl chloride (0.55 g; 3.71 m moles) was added to a solution of alpha-mercaptopropionyl glycine guaiacol ester (1 g; 3.71 m moles) in pyridine (5 ml). The mixture was heated at 50° C. for 2 hours and then allowed to stand at room temperature for 18 hours. The mixture was poured on ice and extracted with methylene chloride. The extract was washed with a saturated aqueous solution of NaHCO$_3$ and thereafter with water to neutrality. The extract was dried over sodium sulfate and evaporated to dryness. The residue, crystallized from ethyl ether, had M.P. 114°–116° C.

(B) The title compound was also prepared with the mixed anhydride method used in Example 6 B for alpha-acetyl mercaptopropionyl guaiacol ester preparation, obtaining the same results.

BIOLOGICAL TESTS

The expectorant and mucolytic activities of alpha-mercaptopropionyl glycine guaiacol ester, alpha-benzoyl-mercaptopropionyl glycine guaiacol ester, alpha-acetyl-mercaptopropionyl glycine guaiacol ester, alpha-methoxycarbonyl mercaptopropionyl glycine guaiacol ester and alpha-mercaptopropionyl alanine guaiacol ester (hereinafter shortly referred to as "ST224", "ST 276", "ST 227", "ST 278" and "ST 279" respectively) were determined.

Expectorant activity

The test was carried out on male rabbits, weighing 2–3 kg, anesthetized with ethyl urethane, by following the method disclosed by Perry et al. (J. Pharm. Exp. Ther. 73, 65, 1941). The anesthetized animals, strapped head downward to an operating table at an inclination of 60°, had a cannula inserted in their trachea. Each cannula was connected to a feeding device which delivered a steady flow-rate of pre-heated air (36°–38° C.) at constant humidity (80%). At the lower end of each cannula, a graduated cylinder was fitted, wherein the bronchial secretion was collected. All of the animals breathed spontaneously and consequently they self-regulated the air intake suitable for normal respiration. After an hour following cannula insertion, the animals were administered either orally (by stomach tube) or intravenously the test compounds dissolved in distilled water (10–100 mg/kg i.v. within 2 minutes). The amount of secretion was determined after administration for 4 hours at 1-hour intervals. The results, summarized in Table 1, show that the test compounds do not exert expectorant activity.

Mucolytic activity

The test was carried out in vitro by using the method disclosed by Morandini et al. (Lotta contro la tubercolosi 47, n. 4, 1977). A thromboelastograph was used to follow the variations induced by the test compounds and acetylcysteine on the rheological properties of human sputum. The results thereof, summarized in Table 2, show that the test compounds bring about a greater decrease of human sputum density than that induced by acetylcysteine.

TABLE 1

| | Effects of ST 224, ST 276, ST 277, ST 278 on bronchial secretions | | | |
|---|---|---|---|---|
| Number of animals | Treatment | Percentage variations ± s.e. of bronchial secretion versus basal values at the following intervals after administration | | |
| | | 1 hour | 2 hours | 4 hours |
| 5 | Controls | +0.9 ± 0.05 | +2.1 ± 0.01 | +3.8 ± 0.09 |
| 5 | ST 224 (10 mg/kg) orally | +1.8 ± 0.04 | +1.7 ± 0.09 | +2.7 ± 0.05 |
| 5 | ST 224 (100 mg/kg) orally | +0.5 ± 0.03 | +0.7 ± 0.07 | +1.9 ± 0.09 |
| 5 | ST 224 (10 mg/kg) intravenously | +2.0 ± 0.08 | +0.5 ± 0.07 | +2.6 ± 0.07 |
| 5 | ST 224 (100 mg/kg) intravenously | +0.4 ± 0.05 | +2.1 ± 0.05 | +1.9 ± 0.04 |
| 4 | Controls | +0.8 ± 0.07 | +1.7 ± 0.05 | +3.7 ± 0.07 |
| 4 | ST 276 (10 mg/kg) intravenously | +2.5 ±0.06 | −2.5 ± 0.07 | +2.5 ± 0.06 |
| 4 | ST 277 (10 mg/kg) intravenously | −1.6 ± 0.06 | −2.7 ± 0.05 | −1.9 ± 0.06 |
| 4 | ST 278 (10 mg/kg) intravenously | +1.7 ± 0.08 | −2.5 ± 0.07 | −1.7 ± 0.09 |

TABLE 2

Mucolytic activity in vitro of ST 224, ST 276, ST 277, ST 278, ST 279 and acetylcysteine.

| In vitro Treatment of sputum | Percentage drop ± s.e. of the tracing versus maximum peak(*) after addition of 1 ml. of a 10% solution of the test compounds at the dilutions indicated | |
|---|---|---|
| | 1/30 | 1/60 |
| ST 224 | 88 ± 9 | 39 ± 6 |
| ST 276 | 79 ± 9 | 42 ± 6 |
| ST 277 | 82 ± 10 | 38 ± 4 |
| ST 278 | 93 ± 9 | 44 ± 7 |
| ST 279 | 87 ± 12 | 44 ± 7 |
| Acetylcysteine | 75 ± 8 | 21 ± 5 |

(*)Mucolytic activity index

Although the daily dose to be administered depends, according to sound professional judgment, upon body weight, age and general conditions exhibited by the patients in need of a mucolytic agent, it has been found that it is generally suitable to administer to said patients from approximately 2.5 mg/kg to approximately 40 mg/kg of body weight per day of the mucolytic agents of this invention. If necessary, higher doses can be safely administered because of the very low toxicity of the guaiacol esters of the invention. For instance, the $LD_{50}$ of ST 224 is 960 (1140–809) mg kg$^{-1}$ e.p.

The pharmaceutical compositions containing the guaiacol esters of the invention can be either solid or liquid can be used in the forms currently used in human medicine, as for example, tablets, lozenges, gelatin capsules, syrups, suspensions, suppositories, injectable preparations, nasal drops, or aerosols. These compositions are prepared in accordance with the usual methods by incorporating the active compounds with the excipients usually used in pharmaceutical compositions, such as talc, gum arabic, lactose, starch, magnesium stearate, aqueous or non-aqueous vehicles, various moistening, dispersing or emulsifying agents, or preservatives.

What is claimed is:

1. A guaiacol ester of a mercaptopropionic acid derivative, selected from the group represented by the general formulae (I) and (II)

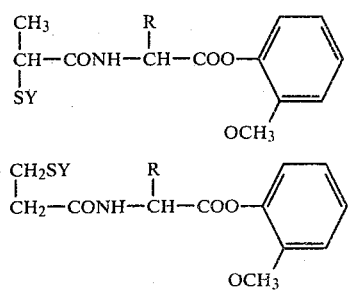

wherein:
R is selected from the group consisting of hydrogen and methyl; and
Y is selected from the group consisting of hydrogen and an alkanoyl aralkanoyl, or benzoyl radical.

2. The guaiacol ester of claim 1, wherein said acyl radical is selected from the group consisting of acetyl, benzoyl and methoxycarbonyl.
3. The guaiacol ester of claim 1, wherein said ester is alpha-mercaptopropionylglycine guaiacol ester.
4. The guaiacol ester of claim 1, wherein said ester is beta-mercaptopropionylglycine guaiacol ester.
5. The guaiacol ester of claim 1, wherein said ester alpha-mercaptopropionylalanine guaiacol ester.
6. The guaiacol ester of claim 1, wherein said ester is beta-mercaptopropionylalanine guaiacol ester.
7. The guaiacol ester of claim 1, wherein said ester is alpha-acetylmercaptopropionylglycine guaiacol ester.
8. The guaiacol ester of claim 1, wherein said ester is beta-acetylmercaptopropionylglycine guaiacol ester.
9. The guaiacol ester of claim 1, wherein said ester is alpha-acetylmercaptopropionylalanine guaiacol ester.
10. The guaiacol ester of claim 1, wherein said ester is beta-acetylmercaptopropionylalanine guaiacol ester.
11. The guaiacol ester of claim 1, wherein said ester is alpha-benzoylmercaptopropionylglycine guaiacol ester.
12. The guaiacol ester of claim 1, wherein said ester is beta-benzoylmercaptopropionylglycine guaiacol ester.
13. The guaiacol ester of claim 1, wherein said ester is alpha-benzoylmercaptopropionylalanine guaiacol ester.
14. The guaiacol ester of claim 1, wherein said ester is beta-benzoylmercaptopropionylalanine guaiacol ester.
15. The guaiacol ester of claim 1, wherein said ester is alpha-methoxycarbonylmercaptopropionylglycine guaiacol ester.
16. The guaiacol ester of claim 1, wherein said ester is beta-methoxycarbonylmercaptopropionylglycine guaiacol ester.
17. The guaiacol ester of claim 1, wherein said ester is alpha-methoxycarbonylmercaptopropionylalanine guaiacol ester.
18. The guaiacol ester of claim 1, wherein said ester is beta-methoxycarbonylmercaptopropionylalanine guaiacol ester.
19. As an intermediate in the preparation of the guaiacol esters of claim 1, a guaiacol ester having the formula:

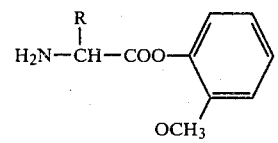

wherein R is selected from the group consisting of hydrogen and methyl.

20. A pharmaceutical composition comprising, as a therapeutically active component, an effective amount of one or more of the guaiacol esters of claim 1 for causing a mucolytic effect to occur in a human patient having a respiratory disease, and containing a pharmaceutically acceptable carrier.
21. A therapeutical method of producing a mucolytic effect in a human patient having a respiratory disease which comprises administering to said patient a mucolytically effective amount of one or more of the guaiacol ester of claim 1.
22. The therapeutical method of claim 21, which comprises administering to said patient from about 2.5 to about 40 mg/kg of body weight daily of a guaiacol ester of claim 1.

* * * * *